United States Patent [19]
Ueda

[11] Patent Number: 5,531,342
[45] Date of Patent: Jul. 2, 1996

[54] PRODUCTION METHOD FOR IMPLANTED HAIR ARTICLES COMPRISING SUPERFINE FIBERS

[76] Inventor: Hiroshi Ueda, 3-16, Imai 3-Chome, Ome-shi, Tokyo, Japan

[21] Appl. No.: 225,718

[22] Filed: Apr. 11, 1994

[30] Foreign Application Priority Data

Mar. 2, 1994 [JP] Japan .................................. 6-056770

[51] Int. Cl.$^6$ ............................... A41G 5/00; B05D 5/00
[52] U.S. Cl. .................... 216/7; 216/41; 216/83; 132/201
[58] Field of Search .............................. 132/201; 216/7, 216/41, 83

[56] References Cited

U.S. PATENT DOCUMENTS

| | | | |
|---|---|---|---|
| 4,613,529 | 9/1986 | Yamashita et al. | 156/72 X |
| 5,005,596 | 4/1991 | Yamada | 132/201 |
| 5,218,977 | 6/1993 | Takahashi | 132/201 X |

Primary Examiner—Thi Dang
Attorney, Agent, or Firm—Lowe, Price, LeBlanc & Becker

[57] ABSTRACT

A production method for implanted hair articles including superfine fibers is disclosed in which the tension and nerve are strong, hair falling is eliminated, and a high grade appearance and flexibility are given. Composite fibers composed of fiber-forming polymers of a plurality of components having an identical or different solubilities for a chemical or solvent are processed into piles P, the piles P are subjected to hair implantation on a face of a base material 4 on which an adhesive for hair implantation is applied and are dried, subsequently a chemical reaction suppressing agent 5 for the above-mentioned chemical or solvent is coated on the hair implantation face of the base material 4, and thereafter the above-mentioned chemical or solvent is used to dissolve and treat components having larger solubilities of the piles P, or each of the components is subjected to a peeling treatment, whereby only portions other than roots of the above-mentioned piles P are divided into each of the polymers.

15 Claims, 4 Drawing Sheets

PRODUCTION METHOD FOR IMPLANTED HAIR ARTICLES COMPRISING SUPERFINE FIBERS

TECHNICAL FIELD

The present invention relates to a production method for implanted hair articles comprising superfine fibers.

BACKGROUND ART

In the prior art, as a production method for implanted hair articles comprising superfine fibers, for example, hair implantation cloth obtained by processing superfine fibers into piles and performing hair implantation of these piles onto base cloth, a method as described below is known.

In such a production method for hair implantation cloth which is obtained such that for example, sea/island type composite fibers, which are composed of two or more kinds of fiber-forming polymers having different solubilities with respect to a chemical or solvent, are processed into piles, and these piles are subjected to hair implantation onto base cloth using an adhesive for hair implantation, and then at least portions of sea components or island components of the piles are dissolved and removed with the chemical or solvent, followed by a heat treatment, namely drying.

FIG. 13 shows a perspective view of the above-mentioned pile 10 made of the sea/island type composite fibers.

The pile 10 made of the sea/island type composite fibers shown in this figure has a structure of the multiple core type in which a plurality of cores 10a of the island component are surrounded by a sheath 10b of the sea component. Both of the sea and island components make the composite, so that when the sea component is dissolved and removed with the chemical or solvent, superfine fibers of only the cores 10a of the island component are obtained as a bundle. With respect to raw materials thereof, for example, polystyrene is used as the sea component, and polyester is used as the island component. Incidentally, the pile 10 made of the sea/island type composite fibers, may be of the parallel type rather than the above-mentioned core/sheath type.

In addition, as the production method for implanted hair articles comprising superfine fibers, rather than the above-mentioned method, there is also known a production method is known in which peeling type composite fibers, in which a plurality kinds (two kinds or three kinds) of fiber-forming polymers are joined by a chemical or solvent in a manner capable of peeling off, are processed into piles. These piles are subjected to hair implantation onto a base material using an adhesive for hair implantation in the same manner as described above, and thereafter the piles are peeled off into each polymer using a chemical or solvent to make the division, or separating of the fibers.

FIG. 14 shows a perspective view of the above-mentioned pile 11 made of the peeling type composite fibers.

The pile 11 made of the peeling type composite fibers shown in this figure is one in which 16 individual hollow composite fibers 11; in of an approximate flower petal shape, are bundled in a radiating form. With respect to the 16 individual composite fibers, nylon fibers 11a and polyester fibers 11b are alternately arranged, in which the nylon fibers 11a are shrunk by means of a chemical treatment, thereby the nylon fibers 11a and the polyester fibers 11b are divided into pieces.

The above-mentioned are representative examples of the known production methods of implanted hair articles comprising superfine fibers.

However, in the case of the above-mentioned pile 10 composed of the composite fibers of the sea/island type, the ultrafine fibers of the island component remaining after the dissolving and removal of the sea component are extremely thin (not more than about 0.05 denier), and the adhesion areas at their roots are extremely small, so that they are easily peeled off upon friction. In addition, short fibers having a lotus root shape composed of the sea component remaining after dissolving of the island component do not provide good feeling even after brushing. Thus, there are such drawbacks that it is impossible to give a unique high grade appearance and flexibility in which the so-called mottling effect and the lighting effect are observed, and products having bad durability of hair implantation are given.

The mottling effect referred to herein means an appearance in which the difference in partial hue (shading of color) or difference in gloss of the standing hair layer generated by irregular orientation (turbulence in hair arrangement) of the standing hairs appears as an amorphous pattern.

In addition, the lighting effect is an appearance effect unique to natural suede, in which the reflecting direction of light changes, and a stroked locus appearance remains on the surface as a result of lying in alignment in a constant direction of standing hairs when the surface having standing hairs is strokes by fingertips.

In addition, there is such a problem that in the case of the above-mentioned pile 10 made of sea/island type composite fibers as a matter of course, even in the case of the pile 11 made of the peeling type composite fibers, when it is subjected to hair implantation on the face of the base material to perform the dissolving or peeling treatment, division is provided up to the root portion of the pile, and thus an implanted hair product having weak tension and nerve.

FIG. 15 shows a front view of the divided pile 10 (11) in such a conventional implanted hair article. As is clear from the same figure, the pile 10 (11) is divided from its root portion 10c (11c), and hence there is a drawback that the divided pile easily suffers from hair fallout. In the same figure, 12 in the figure indicates the base material.

DISCLOSURE OF THE INVENTION

An object of the present invention is to provide a production method for implanted hair articles comprising superfine fibers in which, in order to solve a plurality of problems possessed by the above-mentioned prior art, composite fibers comprising fiber-forming polymers of a plurality of components are processed into piles, are subjected to hair implantation onto a base material, and then before a dissolving treatment or a peeling treatment using a chemical or solvent, a chemical reaction suppressing agent for the above-mentioned chemical or solvent is coated on the pile surface, thereby allowing roots of the above-mentioned piles to remain, while distal portions of the piles can be divided into each polymer.

In order to achieve the above-mentioned object, a method for producing implanted articles comprising superfine fibers of the present invention is characterized in that composite fibers composed of fiber-forming polymers of a plurality of components having an identical or different solubilities for a chemical or solvent are processed into piles, the piles are subjected to hair implantation on a face of a base material, on which an adhesive for hair implantation is applied, and are dried, subsequently a chemical reaction suppressing agent for said chemical or solvent is coated on the hair implantation face of said base material, and thereafter said chemical or solvent is used to dissolve and treat components of the piles having larger solubilities, or each of the components is subjected to a peeling treatment, whereby roots of said piles are allowed to remain, and only distal portions of the piles are divided into each of the polymers.

BEST MODE FOR CARRYING OUT THE INVENTION

Figure 1:
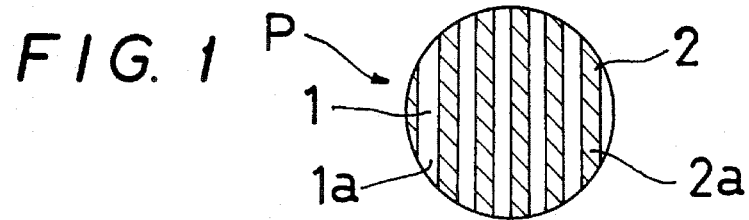
FIG. 1 shows a cross-sectional view of a parallel type of a two component system pile to be used for the present invention.

As the material quality of the fiber-forming polymer for constituting the composite fiber to be used in the present invention, polyamide, polyester, polyolefin and the like are useful. As the polyamide are nylon 6, nylon 11, nylon 12, nylon 66, nylon 610 and polyamides containing them as main components. As the polyester are polyethylene terephthalate, polybutylene terephthalate, polyethylene oxybenzoate, poly-1,4-dimethylcyclohexahen terephthalate, polypivalolactone and copolyesters containing them as main components, and especially polyethylene terephthalate is preferable. As the polyolefin, polyethylene and polypropylene are useful. Polymers other than those described above can be also applied to the present invention provided that they are the fiber-forming polymer.

The composite fiber is cut into a suitable length to prepare piles for hair implantation (short fiber) which are subjected to hair implantation on the substrate, in which the length of the pile is usually 0.3–2.0 mm (preferably 0.5–1.5 mm).

In the present invention, after performing hair implantation using such a composite fiber, the chemical reaction suppressing agent for the chemical or solvent is coated on the surface of the pile, subsequently performing a peeling treatment or the dissolving treatment using the above-mentioned chemical or the like to make fibrillation into a plurality of fibers followed by drying and subsequent brushing, and then it is possible to obtain an implanted hair article in which root portions of the piles are not divided, the contact area with the base material is large, and only upper portions are divided. In addition, it is also available to apply downstream processing such as known flexing and the like. When the chemical reaction suppressing agent in a liquid state is coated on the pile surface, the chemical reaction suppressing agent gradually moves vertically downwardly, and gathers at the pile root portion to form an expanded layer. Owing to the expanded layer, the action of the chemical or solvent is prevented, and the fibrillation of fiber is made only at the forward end and not at the root portion.

As the base material can be exemplified, for example, nonwoven fabric, woven fabric or knitted web containing at least one of a fiber selected from the group consisting of cotton, viscose rayon, acetate fiber, polyamide type fiber and polyester type fiber, or a sheet shape or a shaped article capable of hair implantation processing and downstream processing such as plastic, metal and the like.

The adhesive with which the above-mentioned pile is allowed to adhere to the base material is a known adhesive which is stable against a treating agent and the like, and is capable of providing strong adhesion of the fiber of polyamide and polyester. As such an adhesive, a thermosetting type adhesive is preferable which cures (cross-linking formation, network formation) by heating at a high temperature, and becomes insoluble in hot water, organic solvent, chemical and the like. For example, a mixed composition of a water soluble thermosetting resin such as a melamine-formaldehyde initial condensate, urea-formaldehyde initial condensate and the like, a functional vinyl monomer such as acrylamide, methylolacrylamide, methylenebisacrylamide, glycidyl acrylate, glycidyl methacrylate and the like, and a copolymer comprising acrylic ester or methacrylic ester such as acrylic acid alkyl ester, methacrylic acid alkyl ester, 2-hydroxyalkyl acrylate and the like and acrylic acid and methacrylic acid can be exemplified. Alternatively, methylolated polyamide, polyurethane having an isocyanate group and the like can be also used, however, there is no limitation to those described above. The adhesive is used in a form of a solution or an emulsion.

The hair implantation processing is performed by applying the adhesive onto the base cloth in a uniform thin film form, followed by hair implantation of piles of the composite fiber using a hair implantation machine such as an electrostatic hair implantation machine or the like, and thereafter when the adhesive is cured by heating and drying, then the implanted hair article to be used for the present invention is obtained.

The implanted hair article obtained in such a manner forms a structure in which the piles of the divided fibers are uniformly distributed through the adhesive on the upper face of the base material to give approximately vertical hair standing, which has neither mottling effect nor lighting effect at all.

Next, after the chemical reaction suppressing agent for the chemical or solvent is coated on the pile surface of the implanted hair article, the chemical or solvent is used to make substantial division into each segment. The coating of the chemical reaction suppressing agent onto the pile surface of the implanted hair article is performed using an apparatus such as a dipping spray or the like, and when drying is performed thereafter, the deposit amount is larger at the root portion than at the forward end portion of the pile, and the forward end portion is treated earlier during the following dividing treatment, so that when the treatment is completed before the root portion is divided, an implanted hair article having division from the central portion to the forward end portion in the axial direction of the fiber is obtained. When the deposit amount of the chemical reaction suppressing agent is too great, the division of the pile is difficult to occur in many cases, while when it is too little, there is sometimes such a case in which the chemical or the like swells the adhesive layer, collapse of the pile occurs, and the hair implantation durability is apt to lower.

The chemical reaction suppressing agent referred to herein is such a chemical agent which is not invaded at all by the chemical or solvent during the peeling or dissolving treatment for the pile division, or has resistance in which it takes a time even in the case of invasion, which is coated on the fiber root portion so as to delay the peeling and dissolving of the fiber itself, wherein there is no problem whether or not the layer of the chemical agent remains at the time of completion of treatment, however, when it remains, it facilitates the bulky effect, which is preferable.

The component of the chemical reaction suppressing agent is chosen from those which delay the division of the pile and protect the adhesive layer, for which can be exemplified dimethylpolysiloxane, methylhydrodienepolysiloxane, amino denatured silicon, carboxyl denatured silicon, epoxy denatured silicon, fluorine type macromolecular copolymer, polyvalent alcohol fatty acid ester, polyamine fatty acid amide compound, ester type urethane resin, ether type urethane resin, ester-ether type urethane resin, N-methoxymethylated nylon, special polyester resin and the like.

In addition, it is necessary for the chemical reaction suppressing agent to set the concentration of the component and the like depending on the component, use, length of the pile and the like. With respect to the implanted hair article obtained by coating the chemical reaction suppressing agent, ultimately performing the division treatment and drying, when brushing is performed using a brushing apparatus, the short fibers at the standing hair portions are approximately completely divided, and the implanted hair article of superfine fibers of a high quality having flexible feeling, calm draping, the mottling effect and the lighting effect is obtained.

The piles of the composite fibers composed of fiber-forming polymers of a plurality of components having an identical or different solubilities for the chemical or solvent are subjected to hair implantation on the base material, and before the dissolving treatment or the peeling treatment with the chemical or solvent, the chemical reaction suppressing agent for the above-mentioned chemical or solvent is coated on the hair implantation face of the base material, and thereafter the dissolving treatment or the peeling treatment is performed, so that the root portions of the piles are not divided, and only the portions at the forward end side from the central portions are divided into each polymer.

Therefore, the implanted hair article having strong tension and nerve is obtained because the contact area with the base material is large, the peeling is difficult to occur even upon friction, and hair falling is also difficult to occur.

Examples of the present invention will be explained hereinafter on the basis of the drawings.

FIG. 1 to FIG. 10 show cross-sectional views of piles of the composite fibers of the present invention.

Figure 2:
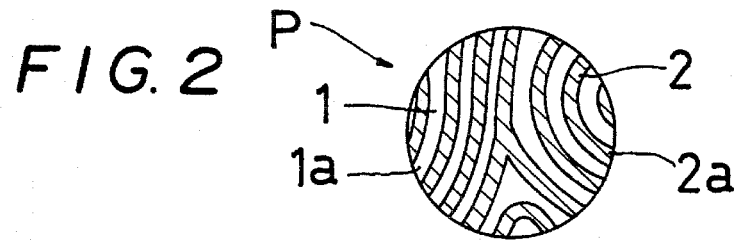
FIG. 2 shows a cross-sectional view of a wood grain type of the two component system pile to be used for the present invention.
Figure 3:
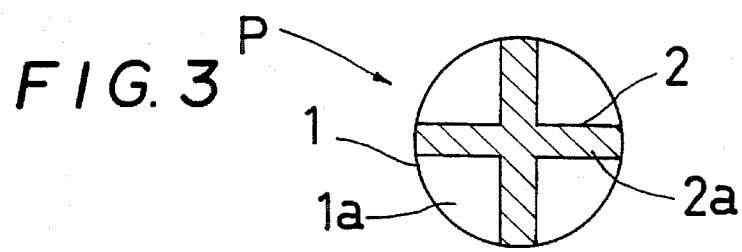
FIG. 3 is a cross-sectional view of a radiating type of the two component system pile to be used for the present invention.
Figure 4:
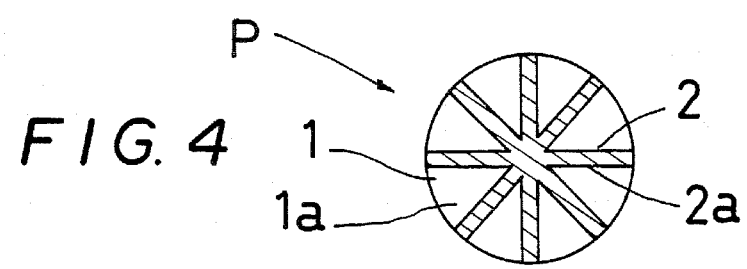
FIG. 4 shows a cross-sectional view of another example of the radiating type of the two component system pile to be used for the present invention.
Figure 5:
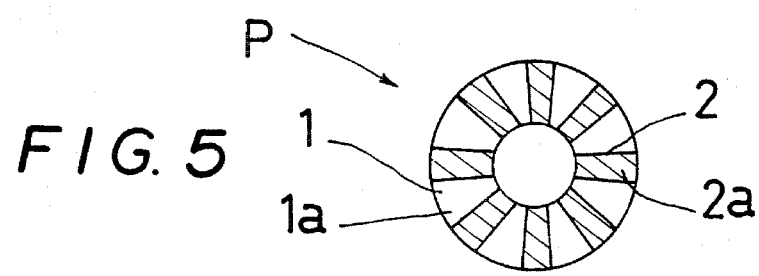
FIG. 5 shows a cross-sectional view of a hollow radiating type of the two component system pile to be used for the present invention.
Figure 6:
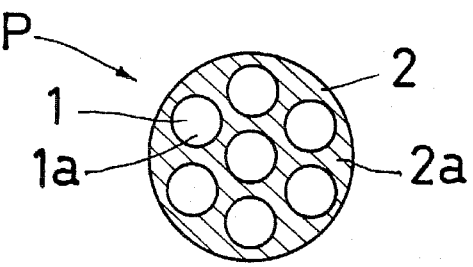
FIG. 6 shows a cross-sectional view of a multiple core type of the two component system pile to be used for the present invention.
Figure 7:
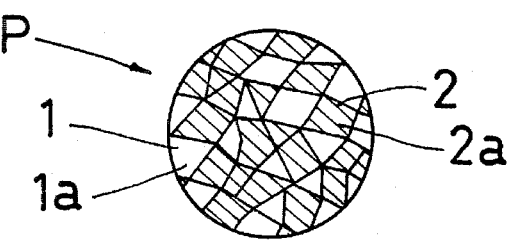
FIG. 7 shows a cross-sectional view of a mosaic type of the two component system pile to be used for the present invention.
Figure 8:
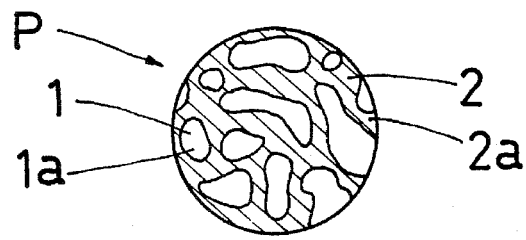
FIG. 8 shows a cross-sectional view of a sea/island type of the two component system pile to be used for the present invention.
Figure 9:
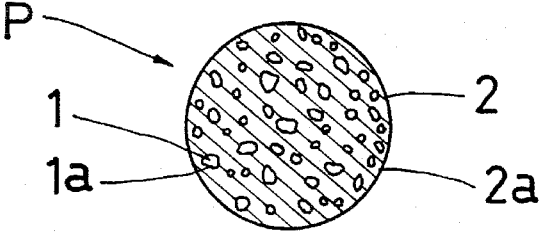
FIG. 9 shows a cross-sectional view of a nebula type of the two component system pile to be used for the present invention.

In particular explanation, FIG. 1 to FIG. 9 show the pile P of the composite fiber as comprising two type of fiber-forming polymers 1, 2, wherein the constitution is made by each of segments 1a, 2a of the parallel type in FIG. 1, of the wood grain type in FIG. 2, of the radiating type in FIG. 3 and FIG. 4, of the hollow radiating type in FIG. 5, of the multiple core type in FIG. 6, of the mosaic type in FIG. 7, of the sea/island type in FIG. 8, and of the nebula type in FIG. 9.

In any one of them, the fiber-forming polymer 2 has a larger solubility than the fiber-forming polymer 1.

Figure 10:
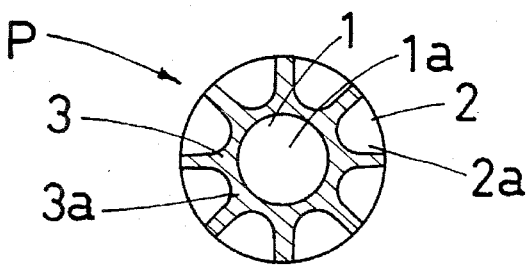
FIG. 10 shows a cross-sectional view of a sector type of a three component system pile to be used for the present invention.

FIG. 10 is a pile P of a composite fiber comprising three kinds of fiber-forming polymers 1, 2 and 3, in which a core segment 1a is arranged at a central portion, and eight flower petal-shaped segments 2a are arranged around it in a surrounding manner.

A segment 3a having the largest solubility intervenes between the core segment 1a and each flower petal-shaped segment 2a.

Figure 11:
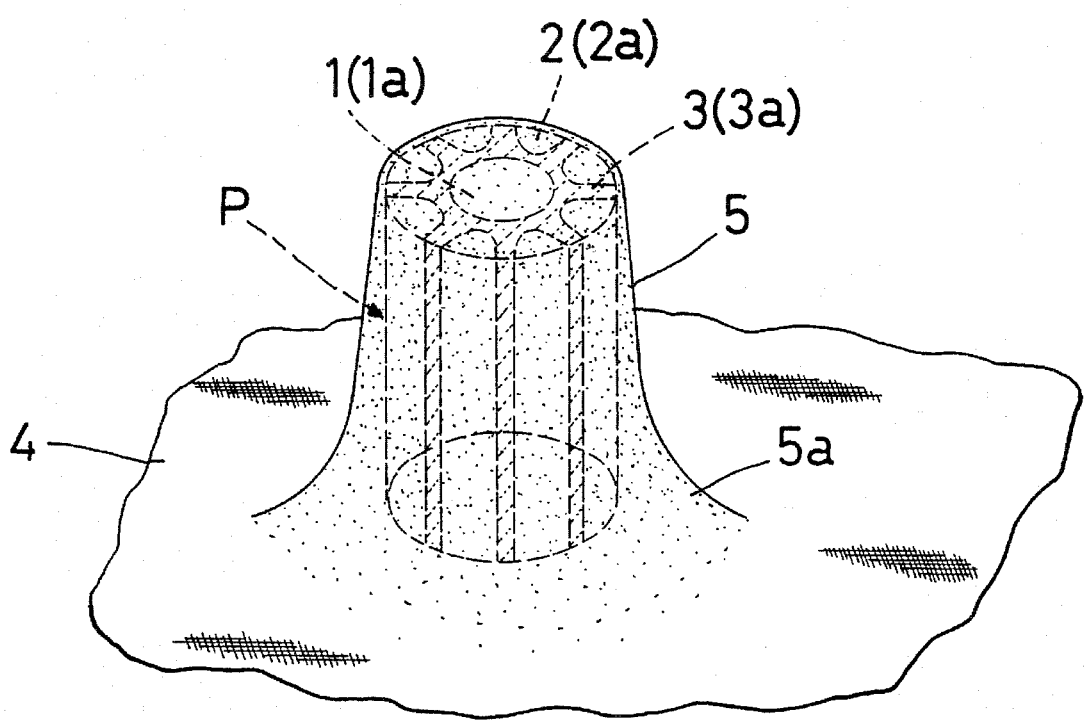
FIG. 11 shows a perspective view of an implanted hair article of the present invention in which the pile in FIG. 10 is used.
Figure 12:
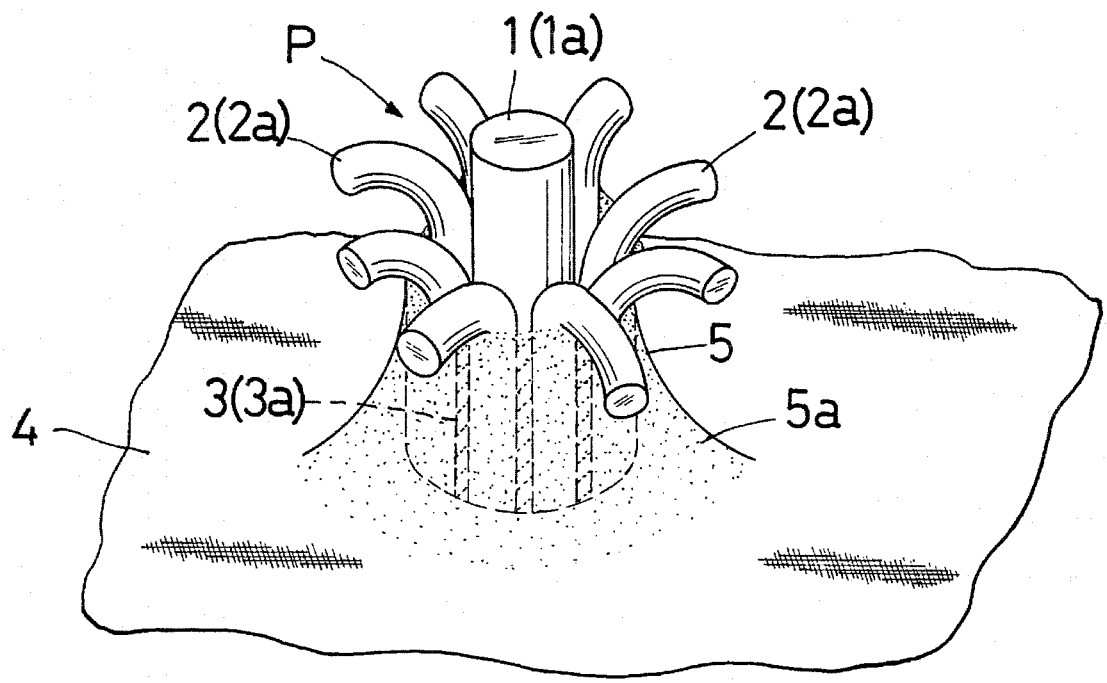
FIG. 12 shows a perspective view of the article of FIG. 11 after division in accordance with the invention.
Figure 13:
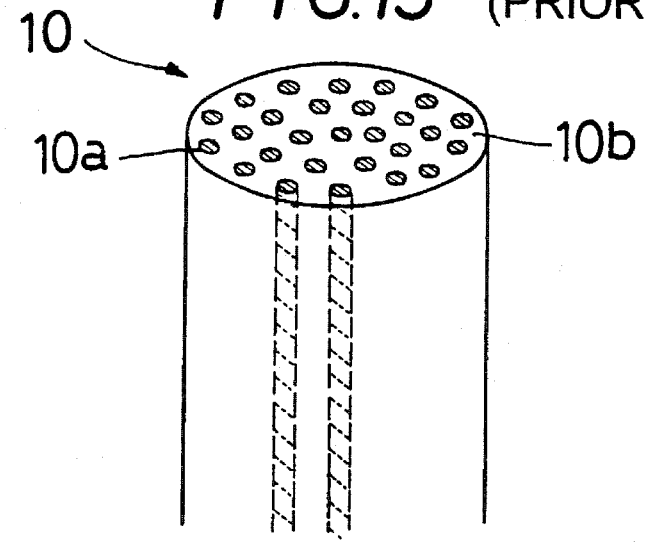
FIG. 13 shows a perspective view of a pile made of conventional sea/island type composite fibers.
Figure 14:
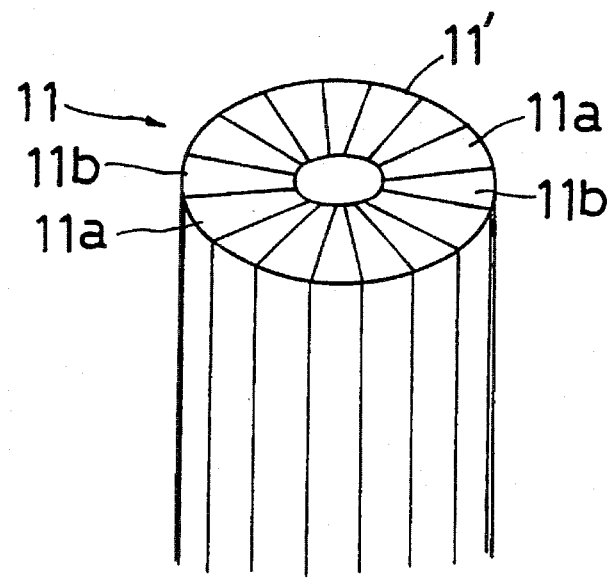
FIG. 14 shows a perspective view of a pile made of conventional peeling type composite fibers.
Figure 15:
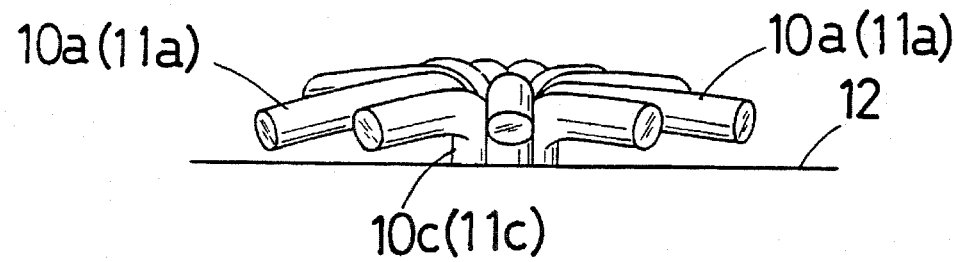
FIG. 15 shows a front view of a conventional implanted hair article.

FIG. 11 shows a perspective view of the implanted hair article of the present invention before division using the pile P in FIG. 10, and FIG. 12 shows a perspective view of the implanted hair article of the present invention after division.

A detailed example of the production method of the implanted hair article of the present invention shown in FIG. 12 is as follows.

The composite fiber having a weaving degree of 3 shown in FIG. 10 was cut into 1.2 mm, which was made into the pile P by performing staining and electrodeposition treatment. 5 parts of a melamine resin and 0.5 part of a cross-linking agent were added to an adhesive containing an acrylic copolymer as a main component, which was coated on rayon base cloth by 300 g/m$^2$, followed by electrostatic hair implantation processing (the up method, voltage: 30 KV, time: 30 seconds) and drying. As the chemical reaction suppressing agent 5 for the chemical or solvent, epoxy denatured silicon was coated by the dipping method, followed by heat treatment (150° C.×1 minute). At this time, the epoxy denatured silicon moved vertically downwardly along the fiber axis of the pile P and remained at the root portion, and an expanded layer 5a was formed on the base cloth 4.

Next, this was subjected to an alkaline treatment (immersion at 80° C. in a 30% NaOH aqueous solution for 8 minutes), and the segment 3a in the pile P was subjected to a dissolving treatment. Thereby with respect to the segments 1a, 2a, only upper forward end portions with respect to the expanded layer 5a were divided.

Finally, a neutralizing agent was used to perform neutralization and washing with water, and brushing was performed after drying to finish to obtain an implanted hair article of superfine fibers.

Incidentally, in the above-mentioned example, the pile P of the composite fibers comprising the three kinds of fiber-forming polymers 1, 2 and 3 shown in FIG. 10 has been used, however, it is also possible to use the piles P of the composite fibers comprising the two kinds of fiber-forming polymers 1, 2 shown in FIG. 1 to FIG. 9. In addition, in the above-mentioned example, the pile P is divided by the dissolving treatment, however, those in which the pile P is divided by a peeling (shrinkage or the like) treatment are also included.

INDUSTRIAL APPLICABILITY

The implanted hair article according to the present invention obtained by the method in the example as described above was such one having unique high grade appearance and flexibility in which the mottling effect and the lighting effect of the superfine fibers were observed. Incidentally, those in which the alkaline treatment was performed under the same condition without forming the expanded film by means of the chemical reaction suppressing agent for the chemical and solvent were those in which the hairs were apt to fall, and collapse of the pile was observed due to the compressive function depending on time.

What is claimed is:

1. A method for producing implanted hair articles comprising superfine fibers wherein composite fibers composed of fiber-forming polymers of a plurality of components having different solubilities for a chemical or solvent are processed into piles, the piles are subjected to hair implantation on a face of a base material on which an adhesive for hair implantation is applied and are dried, subsequently a chemical reaction suppressing agent for said chemical or solvent is coated on the hair implantation face of said base material and on the surface of the piles, the chemical reaction suppressing agent permitted to move vertically downward on the piles toward root portions thereof, and thereafter said chemical or solvent is used to dissolve and treat components of the piles having larger solubilities, or each of the components is subjected to a peeling treatment, whereby roots of said piles are allowed to remain, and distal portions of the piles are divided into each of the polymers.

2. The method for producing implanted hair articles comprising superfine fibers according to claim 1 wherein the base material is nonwoven fabric, woven fabric or knitted web containing at least one of fiber selected from the group consisting of cotton, viscose rayon, acetate fiber, polyamide type fiber and polyester type fiber.

3. The method for producing implanted hair articles comprising superfine fibers according to claim 1 wherein the base material is selected from the group consisting of a sheet shape and a shaped article capable of downstream processing.

4. The method for producing implanted hair articles comprising superfine fibers according to claim 1 wherein the hair implantation is performed by an electrostatic hair implantation method.

5. The method for producing implanted hair articles comprising superfine fibers according to claim 1 wherein the chemical reaction suppressing agent for the chemical or solvent is selected from the group consisting of dimethylpolysiloxane, methylhydrodienepolysiloxane, amino denatured silicon, carboxyl denatured silicon, epoxy denatured silicon, fluorine type macromolecular copolymer, polyvalent alcohol fatty acid ester, polyamine fatty acid amide compound, ester type urethane resin, ether type urethane resin, ester-ether type urethane resin, N-methoxymethylated nylon and special polyester resin and a composite thereof.

6. The method for producing implanted hair particles comprising superfine fibers according to claim 1 wherein the base material is a sheet shape capable of a downstream processing step selected from the group consisting of hair implantation processing and dividing treatment.

7. The method for producing implanted hair particles comprising superfine fibers according to claim 1 wherein the base material is a shaped article capable of a downstream processing step selected from the group consisting of hair implantation processing and dividing treatment.

8. The method for producing implanted hair particles comprising superfine fibers according to claim 1 wherein the base material is selected from the group consisting of plastic and metal.

9. The method for producing implanted hair particles comprising superfine fibers according to claim 8 wherein the base material is capable of a downstream processing step selected from the group consisting of hair implantation processing and dividing treatment.

10. The method for producing implanted hair particles comprising superfine fibers according to claim 1 wherein the base material is capable of a downstream processing step selected from the group consisting of hair implantation processing and dividing treatment.

11. A method for producing implanted hair articles having superfine fibers, comprising the steps of:

processing a plurality of piles including a plurality of fiber-forming polymers as components thereof, performing a hair implantation of the piles on a face of a base material, and thereafter dividing the piles to separate components at portions distal from respective root portions while maintaining the root portions in piles, by:
coating on the piles a chemical reaction suppressing agent for suppressing a reaction between the fiber-forming polymers and a solvent,
wherein said coating step comprises forming an expanded layer of the chemical reaction suppressing agent on the hair implantation face of said base material by permitting the chemical reaction suppressing agent to move vertically downward on the piles toward the root portions thereof, thereby preventing division of the piles at said root portions, and
thereafter using said solvent to dissolve at least one of the fiber-forming polymers of the piles, thereby dividing only distal portions of the piles into the separate components while maintaining the root portions of the piles in piles.

12. The method of claim 11, wherein the plurality of fiber-forming polymers of said piles have substantially identical solubilities for the solvent.

13. The method of claim 11, wherein the plurality of fiber-forming polymers of said piles have different solubilities for the solvent.

14. A method for producing implanted hair articles having superfine fibers, comprising the steps of:

processing a plurality of piles including a plurality of fiber-forming polymers having different solubilities for a solvent, subjecting the piles to hair implantation on a face of a base material, subsequently coating on the hair implantation face of said base material and on the surface of the piles a chemical reaction suppressing agent for suppressing a reaction between the fiber-forming polymers and said solvent, permitting the chemical reaction suppressing agent to move vertically downward on the piles toward root portions thereof, and thereafter using said solvent to dissolve and treat the fiber-forming polymers of the piles having larger solubilities thereby dividing only distal portions of the piles into the polymers while maintaining undivided the root portions of the piles.

15. A method for producing implanted hair articles comprising superfine fibers wherein composite fibers composed of fiber-forming polymers of a plurality of components having substantially identical solubilities for a chemical or solvent are processed into piles, the piles are subjected to hair implantation on a face of a base material on which an adhesive for hair implantation is applied and are dried, subsequently a chemical reaction suppressing agent for said chemical or solvent is coated on the hair implantation face of said base material and on the surface of the piles, the chemical reaction suppressing agent permitted to move vertically downward on the piles toward root portions thereof, and thereafter said chemical or solvent is used to dissolve and treat the components of the piles, or each of the components is subjected to a peeling treatment, whereby roots of said piles are allowed to remain, and distal portions of the piles are divided into each of the polymers.

* * * * *